United States Patent
Hayashizaki et al.

(10) Patent No.: US 6,428,670 B1
(45) Date of Patent: Aug. 6, 2002

(54) GEL CHARGER FOR CAPILLARY COLUMN

(75) Inventors: Yoshihide Hayashizaki, Ibaraki; Rintaro Yamamoto, Kyoto, both of (JP)

(73) Assignees: The Institute of Physical and Chemical Research, Saitama; Shimadzu Corporation, Kyoto, both of (JP)

( * ) Notice: Subject to any disclaimer, the term of this patent is extended or adjusted under 35 U.S.C. 154(b) by 0 days.

(21) Appl. No.: 09/443,720

(22) Filed: Nov. 19, 1999

(30) Foreign Application Priority Data

May 12, 1999 (JP) .......................................... 11-130815

(51) Int. Cl.$^7$ ........................ C25B 15/08; B01D 57/02; C25F 7/02; C02F 1/469; C25D 21/16
(52) U.S. Cl. ...................... 204/601; 204/451; 204/453; 204/455; 204/604; 204/605
(58) Field of Search ................................ 204/451, 453, 204/455, 601, 604, 605

(56) References Cited

U.S. PATENT DOCUMENTS

| | | | | |
|---|---|---|---|---|
| 5,277,780 A | * | 1/1994 | Kambara | 204/299 |
| 5,366,608 A | * | 11/1994 | Kambara | 204/299 |
| 5,439,578 A | * | 8/1995 | Dovichi et al. | 204/299 |
| 5,468,364 A | * | 11/1995 | Fujii | 204/299 |
| 5,516,409 A | * | 5/1996 | Kambara | 204/603 |
| 5,541,420 A | * | 7/1996 | Kambara | 204/602 |
| 5,560,811 A | * | 10/1996 | Briggs et al. | 204/451 |
| 5,667,656 A | * | 9/1997 | Kambara | 204/603 |
| 5,695,626 A | * | 12/1997 | Yeung et al. | 204/605 |
| 5,885,430 A | * | 3/1999 | Kernan et al. | 204/453 |
| 5,916,428 A | * | 6/1999 | Kane et al. | 204/601 |
| 5,968,331 A | * | 10/1999 | Kambara et al. | 204/450 |
| 6,017,765 A | * | 1/2000 | Yamada et al. | 436/47 |
| 6,027,627 A | * | 2/2000 | Li et al. | 204/603 |
| 6,048,444 A | * | 4/2000 | Takahashi et al. | 204/603 |
| 6,063,251 A | * | 5/2000 | Kane et al. | 204/601 |
| 6,093,300 A | * | 7/2000 | Hayashizaki et al. | 204/604 |
| 6,162,341 A | * | 12/2000 | Nordman et al. | 204/603 |

OTHER PUBLICATIONS

Bartosiewicz et al., "Implementation of a capillary array electrophoresis instrument," ISC Technical Publications, Inc. Feb. 1996, pp. 61–68.*
Clark et al., High–Speed Parallel Separation of DNA Restriction Fragments Using Capillary Array Electrophoresis, Anal. Biochemistry 215, 1993, pp. 163–170.*
Huang et al., "Capillary Array Electrophoresis Using Laser–Excited Confocal Fluorescence Detection," Anal. Chem.vol. 64, 1992, pp. 968–972.*
Huang et al., "DNA Sequencing Using Capillary Array Electrophoresis," Anal. Chem., vol. 64, 1992, pp. 2149–2154.*
Takahashi et al., "Multiple Sheath–Flow Gel Capillary–Array Electrophoresis for Multicolor Fluorescent DNA Detection," Anal. Chem. 1994, 66, pp. 1021–1026.*
Ueno et al., "Simultaneous Monitoring of DNA Fragments Separated by Electrophoresis in a Multiplexed Array of 100 Capillaries," Anal. Chem. 66, 1994, pp. 1424–1431.*

* cited by examiner

*Primary Examiner*—Jill Warden
*Assistant Examiner*—Jennine Brown
(74) *Attorney, Agent, or Firm*—Rader, Fishman & Grauer, PLLC (57) ABSTRACT

A holder for a capillary cassette closes a chamber, and is fixed to a detection side holder fixing member. An acidic solution container, an alkaline solution container, a pure water container and a drain container are arranged on a reservoir stage having a dry chamber. A holder up/down mechanism and a stage moving mechanism successively bring an end of a capillary array into contact with an acidic solution, an alkaline solution, pure water and nitrogen gas, and the chamber is decompressed for successively introducing these into capillary columns and performing pretreatment. Thereafter a gel container is arranged in the chamber, which in turn is pressurized for charging the capillary columns with a gel.

17 Claims, 7 Drawing Sheets

GEL CHARGER FOR CAPILLARY COLUMN

BACKGROUND OF THE INVENTION

1. Field of the Invention

The present invention relates to a gel charger for charging a plurality of capillary columns used in a multi-capillary electrophoretic apparatus with a gel serving as a medium for electrophoresing samples.

2. Description of the Prior Art

An electrophoretic apparatus is used for separating and analyzing protein, peptide, sugar or the like, and plays an important part particularly for analysis of the base sequence of DNA.

A DNA sequencer having high sensitivity, a high speed and high throughput is necessary for sequence determination for DNA such as a human genome having long base sequence. As an example, a multi-capillary electrophoretic apparatus formed by arranging a plurality of capillary columns charged with a gel in place of a flat plate type slab gel is proposed. With such capillary columns, samples can not only be readily handled or injected but also electrophoresed at a high speed, and detected in high sensitivity as compared with the slab gel. If a high voltage is applied to the slab gel, a band is spread or a temperature gradient is caused due to influence by Joulean heat However, the capillary columns hardly cause such a problem and can perform detection in high sensitivity with small band spreading even if performing high-speed electrophoresis with application of a high voltage.

Capillary gel electrophoresis using a supporter (separation medium) having a molecular sieving effect in a glass capillary column having an inner diameter of 10 to 200 $\mu$m separates nucleic acid or protein by the molecular sieving effect of the separation medium. The separation medium is formed by cross-liked polyacrylamide prepared by polymerizing a cross-linking gel in the capillary column or a previously polymerized high polymer such as linear polyacrylamide or hydroxyethyl cellulose charged into the capillary column.

An initial capillary electrophoretic apparatus employs a single capillary column. In this case, an end of the capillary column is dipped in a gel stored in a container, which in turn is closed and pressurized for forcing and charging the gel into the capillary column. Alternatively, an end of the capillary column is dipped in the gel and another end of the capillary column is decompressed for sucking and charging the gel into the capillary column.

In a multi-capillary electrophoretic apparatus, a plurality of capillary columns are mounted on the multi-capillary electrophoretic apparatus in a state two-dimensionally arranged on a sample injection side and aligned with each other on a plane on a detection side. The plurality of capillary columns are preferably set in a capillary cassette in which the arrangement is fixed by a holder, in consideration of operability.

It is extremely troublesome and impossible in practice to charge the capillary columns one by one with a gel in the state of the capillary cassette. Therefore, it is desired to make it possible to readily charge all capillary columns included in a unit capillary cassette with the gel.

In relation to a separation medium polymerizing a gel in a capillary column, the state of the inner wall surface of the capillary column influences the polymerized state of the gel. If the state of the inner wall surface is inferior, the polymerized state of the gel is deteriorated to increase the frequency of generating bubbles in the capillary column during electrophoresis. Furthermore, if the state of the inner wall surface is inferior, frequency that the gel comes out from an end of the capillary column on a sample injection side is increased whether or not the gel is a cross-linked gel or a high polymer. Thus, reproducibility of an electrophoresis result is disadvantageously deteriorated.

While pretreatment of introducing an acidic solution into the capillary column or the like must be performed for solving this problem, it is extremely troublesome and impossible in practice to pretreat each capillary column contained in a capillary cassette.

SUMMARY OF THE INVENTION

Accordingly, an objective of the present invention is to provide a gel charger capable of readily pretreating and charging all capillary columns contained in a capillary cassette with a gel and improving reproducibility of an electrophoresis result in capillary electrophoresis.

The present invention is directed to an apparatus for charging a plurality of capillary columns of a capillary cassette, in which ends of the capillary columns, mounted on a multi-capillary electrophoretic apparatus, on a sample injection side are two-dimensionally arranged through a holding member of a holder and fixed with airtightness between the same and the holding member with a gel.

The capillary columns can be charged with the gel by either suction or pressurization. When charged with the gel, the capillary columns are not sealed one by one and subjected to suction or pressurization, but the holder airtightly fixing the capillary columns seals all capillary columns of the capillary cassette to charge all capillary columns with the gel simultaneously.

A number of silanol groups (—SiOH) are present on inner wall surfaces of glass capillary columns. The states of the silanol groups vary with the capillary columns. The states of the silanol groups remarkably influence a polymerized state of the gel, and hence the difference between the states of the silanol groups varying with the capillary columns vary the polymerized state of the gel.

Therefore, the apparatus according to the present invention introduces acid into the capillary columns before charging the same with the gel or a polymer for arranging the states of the silanol groups on the inner wall surfaces of the capillary columns (hereinafter referred to as acid treatment) and bringing the silanol groups into states suitable for gel polymerization. Consequently, the polymerized state of the gel in the capillary columns can be stabilized. On the other hand, acid inhibits gel polymerization and hence the capillary columns subjected to acid treatment are thereafter washed with pure water. If moisture remains in the capillary columns, gel polymerization is inhibited or the gel concentration is reduced. As a result, the capillary columns are dried with inert gas.

In a system performing gel charging by suction, a gel charger according to the present invention comprises a chamber airtightly fixing ends of capillary columns on a sample injection side, an inert gas supply mechanism supplying inert gas, decompression means decompressing the chamber, and an introduced substance selection mechanism for supplying ends of the capillary columns on a detection side opposite to the sample injection side with inert gas, an acidic solution, pure water or a gel. The chamber is provided on its upper surface with an opening, which in turn is provided with closure means receiving the ends of the capillary columns on the sample injection side therein and closing the opening with a holder, and a gas outlet is further provided. The decompression means is provided on the gas outlet of the chamber. The introduced substance selection mechanism comprises an inert gas supply port supplied with inert gas from the inert gas supply mechanism, an acidic solution container storing an acidic solution, a pure water container storing pure water and a gel container storing a gel, and comprises a mechanism moving the inert gas supply port, the acidic solution container, the pure water container and the gel container as well as ends of the capillary columns on a detection side opposite to the sample injection side so that the ends of the capillary columns on the detection side are inserted in any of the inert gas supply port, the acidic solution container, the pure water container and the gel container.

In operation, the gel charger closes the opening of the chamber with the closure means through the holder of the capillary cassette thereby fixing the detection side of the capillary cassette to the introduced substance selection mechanism. Then the gel charger arranges the acidic solution container, the pure water container, the gel container and the inert gas supply port on prescribed positions of the introduced substance selection mechanism.

First, the introduced substance selection mechanism dips forward ends of all capillary columns on the detection side of the capillary cassette in the acidic solution stored in the acidic solution container while the decompression means decompresses the chamber for inhaling the acidic solution into the capillary columns and performing acid treatment on the inner wall surfaces of the capillary columns.

Secondly, the introduced substance selection mechanism dips the forward ends of all capillary columns on the detection side of the capillary cassette in the pure water stored in the pure water container while the decompression means decompresses the chamber for inhaling the pure water into the capillary columns and discharging the acidic solution from the capillary columns.

Thirdly, the introduced substance selection mechanism inserts the forward ends of all capillary columns on the detection side of the capillary cassette into the inert gas supply port for supplying the inert gas from the inert gas supply mechanism and the decompression means decompresses the chamber for inhaling the inert gas into the capillary columns and drying the capillary columns.

Lastly, the introduced substance selection mechanism dips the forward ends of all capillary columns on the detection side of the capillary cassette in the gel stored in the gel container while the decompression means decompresses the chamber for inhaling the gel into the capillary columns. Thus, gel charging is completed.

In a system performing gel charging by pressurization, a gel charger according to the present invention comprises a chamber fixing ends of capillary columns on a sample injection side while keeping airtightness and storing a gel therein, a gel container, storing the gel, detachably arranged in the chamber, pressurization/decompression means pressurizing or decompressing the chamber, an inert gas supply mechanism supplying inert gas, and an introduced substance selection mechanism for supplying ends of the capillary columns on a detection side opposite to the sample injection side with inert gas, an acidic solution or pure water or connecting the same to a drain. The chamber is provided on its upper surface with an opening, which in turn is provided with closure means receiving the ends of the capillary columns on the sample injection side therein and closing the opening with a holder, and a gas outlet is further provided.

The pressurization/decompression means is provided on the gas outlet of the chamber. The gel container is so arranged in the chamber that the gel comes to a position where the ends of the capillary columns on the sample injection side are dipped while the opening of the chamber is closed with the holder. The introduced substance selection mechanism comprises an inert gas supply port supplied with inert gas from the inert gas supply mechanism, an acidic solution container storing an acidic solution, a pure water container storing pure water and a drain container, and comprises a mechanism moving the inert gas supply port, the acidic solution container, the pure water container and the drain container as well as the ends of the capillary columns on the detection side so that ends of the capillary columns on a detection side opposite to the sample injection side are inserted in any of the inert gas supply port, the acidic solution container, the pure water container and the drain container.

In operation, the gel charger of this system closes the opening of the chamber with the closure means through a holder of a capillary cassette while not arranging the gel container in the chamber. The gel charger fixes a detection side of the capillary cassette to the introduced substance selection mechanism, and arranges the acidic solution container, the pure water container, the inert gas supply port and the drain container on prescribed positions of the introduced substance selection mechanism.

First, the introduced substance selection mechanism dips forward ends of all capillary columns on the detection side of the capillary cassette in the acidic solution stored in the acidic solution container while the pressurization/decompression mechanism decompresses the chamber for inhaling the acidic solution into the capillary columns and performing acid treatment on inner wall surfaces of the capillary columns.

Secondly, the introduced substance selection mechanism dips the forward ends of all capillary columns on the detection side of the capillary cassette in the pure water stored in the pure water container while the pressurization/decompression mechanism decompresses the chamber for inhaling the pure water into the capillary columns and discharging the acidic solution from the capillary columns.

Thirdly, the introduced substance selection mechanism inserts the forward ends of all capillary columns on the detection side of the capillary cassette into the inert gas supply port and supplies the inert gas from the inert gas supply mechanism, while the pressurization/decompression mechanism decompresses the chamber for inhaling the inert gas into the capillary columns and drying the capillary columns.

Lastly, the holder is temporarily detached from the opening of the chamber, the gel container is arranged in the chamber and thereafter the opening of the chamber is closed with the holder again. Thereafter the introduced substance selection mechanism inserts the forward ends of all capillary columns on the detection side of the capillary cassette in the drain container while the pressurization/decompression means pressurizes the chamber for injecting the gel into the capillary columns. The drain container receives an excess amount of gel overflowing the ends of the capillary columns on the detection side.

When a plurality of columns forming a capillary array mounted on a multi-capillary electrophoretic apparatus are charged with a gel solution, the respective capillary columns are not directly closed and fixed but sealed with the closure means and charged with the gel through a sample injection side cassette holder airtightly fixing the plurality of capillary columns, whereby the plurality of capillary columns can be simultaneously charged with the gel. Simplicity of mounting and airtightness in mounting can be compatibly attained.

The plurality of capillary columns can be simultaneously charged with the gel solution, whereby the maximum merit of improving the throughput by simultaneously electrophoresing a plurality of samples in multi-capillary electrophoresis is not damaged by a process of gel charge serving as pretreatment of the electrophoresis Furthermore, the acidic solution arranges states of silanol groups on the inner wall surfaces of the capillary columns, whereby the states of the inner wall surfaces of the capillary columns can be optimized in relation to gel charging and gel polymerization. Consequently, a polymerized state in gel polymerization is improved, a bubble generation ratio in application of an electrophoresis voltage is reduced and displacement of the gel is reduced, whereby reproducibility of a electrophoresis result can be improved.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

When a glass capillary column is repeatedly used, dirt such as a residue of a gel in previous measurement may adhere to the inner wall surface of the capillary column. If a gel is polymerized in the capillary column as such in this case, the polymerized state of the gel is deteriorated.

Therefore, before charging the capillary column with the gel, an alkaline solution is preferably introduced into the capillary column for removing the dirt adhering to the inner wall surface of the capillary column (hereinafter referred to as alkali treatment). Consequently, the polymerized state of the gel in the capillary column can be stabilized. On the other hand, the alkaline solution also inhibits polymerization of the gel, and hence the capillary column is washed with pure water after the alkali treatment If moisture remains in the capillary column, gel polymerization is inhibited or the gel concentration is reduced causing the capillary column to be dried with inert gas in this case as well.

Therefore, in the system performing gel charging by suction, the introduced substance selection mechanism according to the present invention preferably further comprises an alkaline solution container storing an alkaline solution, and moves the inert gas supply port, the acidic solution container, the alkaline solution container, the pure water container and the gel container as well as the ends of the capillary columns on the detection side so that the ends of the capillary columns on the detection side are dipped into the inert gas supply port, the acidic solution container, the alkaline solution container, the pure water container, or the gel container.

In the system performing gel charging by pressurization, the introduced substance selection mechanism according to the present invention preferably further comprises an alkaline solution container storing an alkaline solution and moves the inert gas supply port, the acidic solution container, the alkaline solution container, the pure water container and the drain container as well as the ends of the capillary columns on the detection side so that the ends of the capillary columns on the detection side are dipped into the inert gas supply port, the acidic solution container, the alkaline solution container, the pure water container, or the drain container.

In each of the systems performing gel charging by suction and by pressurization, the introduced substance selection mechanism dips the forward ends of all capillary columns on the detection side of the capillary cassette in the alkaline solution stored in the alkaline solution container before or after acid treatment and before gel charging and the decompression means or the pressurization/decompression means decompresses the chamber for inhaling the alkaline solution into the capillary columns and performing alkali treatment on the inner wall surfaces of the capillary columns.

Thereafter the pure water is inhaled into the capillary columns for discharging the alkaline solution from the capillary columns, and the inert gas is inhaled for drying the capillary columns. Thereafter gel charging is performed by pressurization or suction similarly to the aforementioned gel charging operation.

When performing both of the alkali treatment and the acid treatment, gel charging is performed by pressurization or suction after performing the aforementioned alkali treatment, acid treatment, washing and drying.

When comprising a plurality of chambers for sharing the decompression means or the pressurization/decompression means by the plurality of chambers, the inert gas supply port of the introduced substance selection mechanism, the acidic solution container, the alkaline solution container, the pure water container, the drain container or/and the gel container are preferably shared as to the capillary columns mounted on different chambers. Consequently, a plurality of capillary cassettes can be simultaneously subjected to pretreatment and gel charging, while the structure of the overall apparatus can be simplified.

It is preferable to comprise a control part automatically controlling operations of the inert gas supply mechanism, the introduced substance selection mechanism and the decompression means or the pressurization/decompression means for controlling exchange of the container for receiving the ends of the capillary columns, introduction of the ends of the capillary columns into the container and operations of the decompression means or the pressurization/decompression means and the inert gas supply mechanism in pretreatment and gel charging by the control part and automatically performing pretreatment and gel charging. Consequently, the labor of an operator can be saved.

Figure 1:
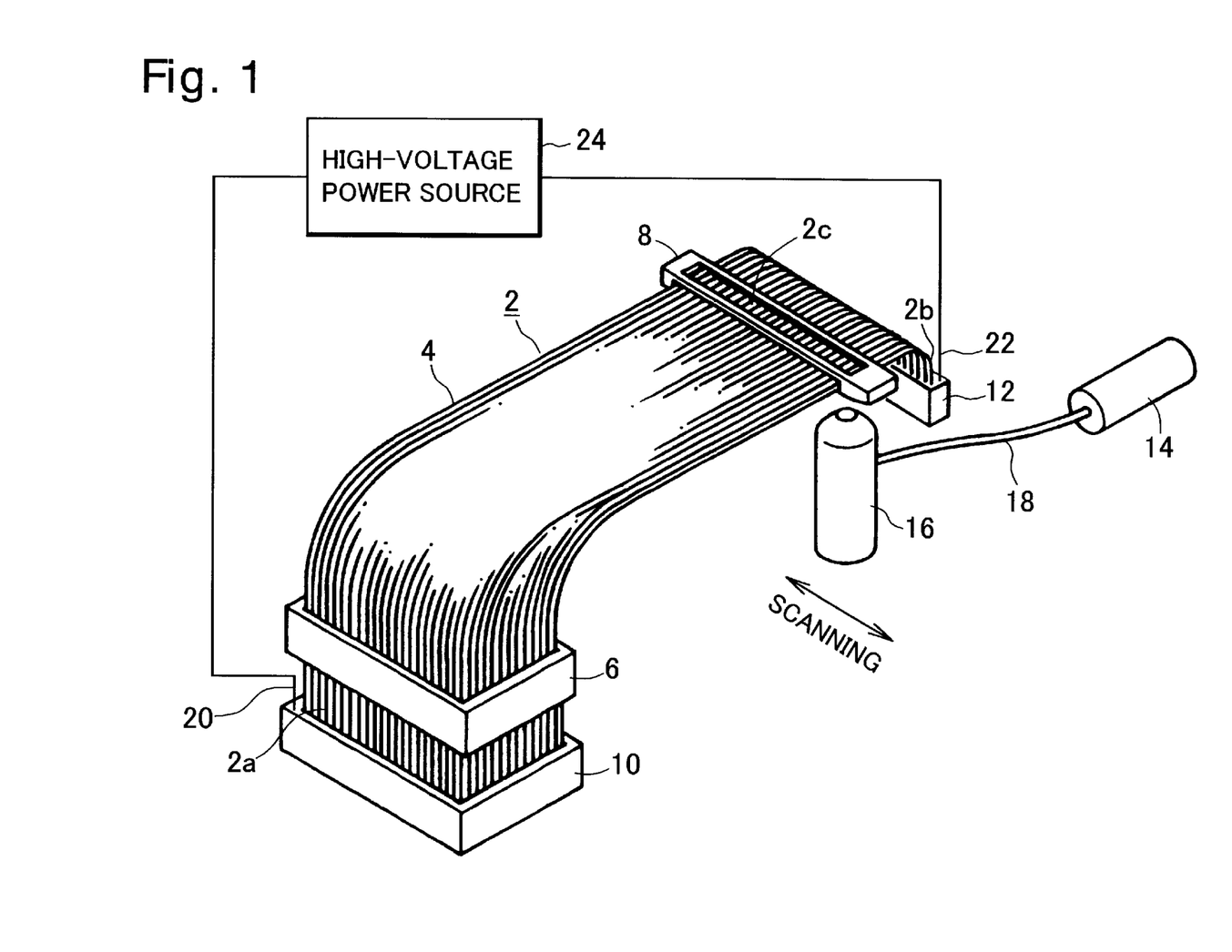
FIG. 1 is a schematic perspective view of an exemplary multi-capillary electrophoretic apparatus on which a capillary cassette charged with a gel according to the present invention is mounted.

FIG. 1 is a schematic perspective view showing an exemplary multi-capillary electrophoretic apparatus.

In a capillary cassette, a plurality of, e.g., 384 capillary columns 4 are arranged and fixed by a sample injection side holder 6 and a detection side holder 8 to form a capillary array 2. An end 2a of the capillary array 2 defines a sample injection side where the capillary columns 4 are two-dimensionally arranged in 16 rows by 24 columns by the sample injection side holder 6 and fixed to come into contact with a buffer solution for electrophoresis stored in a electrophoresis reservoir 10 after sample injection. The capillary columns 4 are aligned with each other on a terminal end (detection side end) 2b of the capillary array 2 to come into contact with a buffer solution stored in another reservoir 12. On a detected part 2c closer to the terminal end 2b of the capillary array 2, the capillary columns 4 are aligned with each other and supported by the detection side holder 8.

The capillary columns 4 are covered with coating, to be protected against breakage. When fluorescence detection is employed for detecting electrophoresing samples and the coatings generate fluorescence, the coatings are removed on the detected part 2c. However, if the capillary columns 4 are covered with coatings of a non-fluorescent material, the coatings do not have to be removed on the detected. part 2c.

Different samples are injected into the capillary columns 4 respectively, to be simultaneously electrophoresed.

An argon gas laser unit, for example, is provided as an excitation light source 14 for exciting the samples or a fluorescent material labeling the samples. Numeral 16 denotes an excitation and photoreceiving optical system, which applies an excitation light beam to the capillary columns 4 on the detected part 2c and detects fluorescence from the samples. The excitation and photoreceiving optical system 16 is scanned by a scanning mechanism (not shown) in a scanning direction, as indicated by the arrow, parallel to the plane of arrangement of the capillary columns 4 on the detected part 2c and perpendicular to the electrophoresis direction. The laser beam from the excitation light source 14 is guided to the excitation and photoreceiving optical system 16 through an optical fiber member 18 coupled by for example a coupler, so that the excitation light beam will not deviate by scanning of the excitation and photoreceiving optical system 16.

The reservoir 10 stores the buffer solution so that the end 2a of the capillary array 2 defining the sample injection side is dipped in the buffer solution and a electrophoresis voltage is applied to ends of the capillary columns 4 forming the end 2a of the capillary array 2 through the buffer solution. The reservoir 12 also stores the buffer solution, so that the terminal end 2b of the capillary array 2 defining the detection side is dipped in the buffer solution and the electrophoresis voltage is applied to ends of the capillary columns 4 forming the terminal end 2b of the capillary array 2 through the buffer solution. An upper electrode 22 is dipped in and comes into contact. with the buffer solution of the reservoir 12 and a lower electrode 20 is dipped in and comes into contact with the buffer solution of the reservoir 10, while a high-voltage power source 24 applies the electrophoresis voltage to the electrodes 20 and 22. A power supply voltage thereof is 30 kV, for example, and a current capacity is 10 to 30 mA.

The samples to be electrophoresed are proteins or DNA fragments labeled with a fluorescent material.

Figure 2:
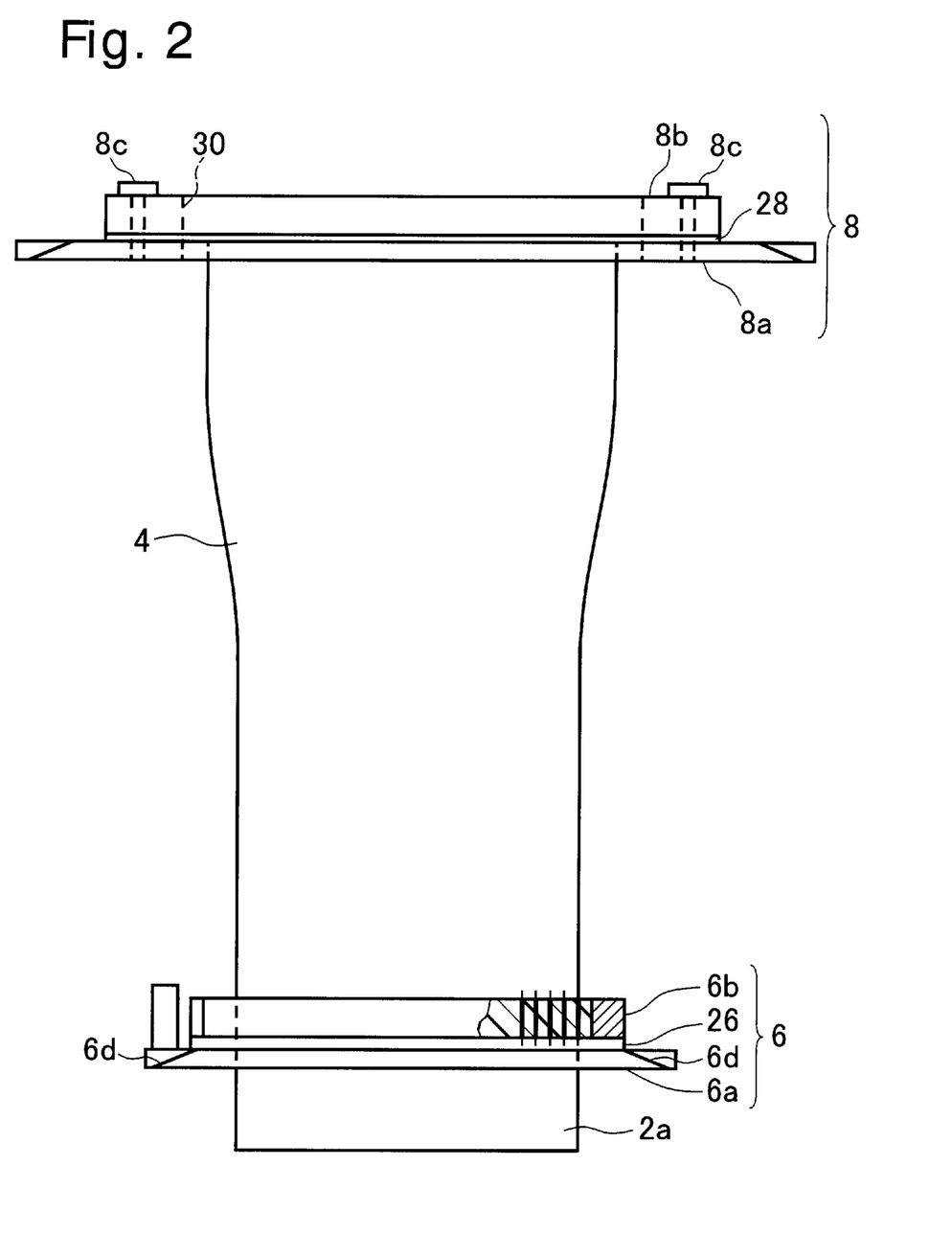
FIG. 2 is a front elevational view of an exemplary capillary cassette charged with a gel according to the present invention.
Figure 3:
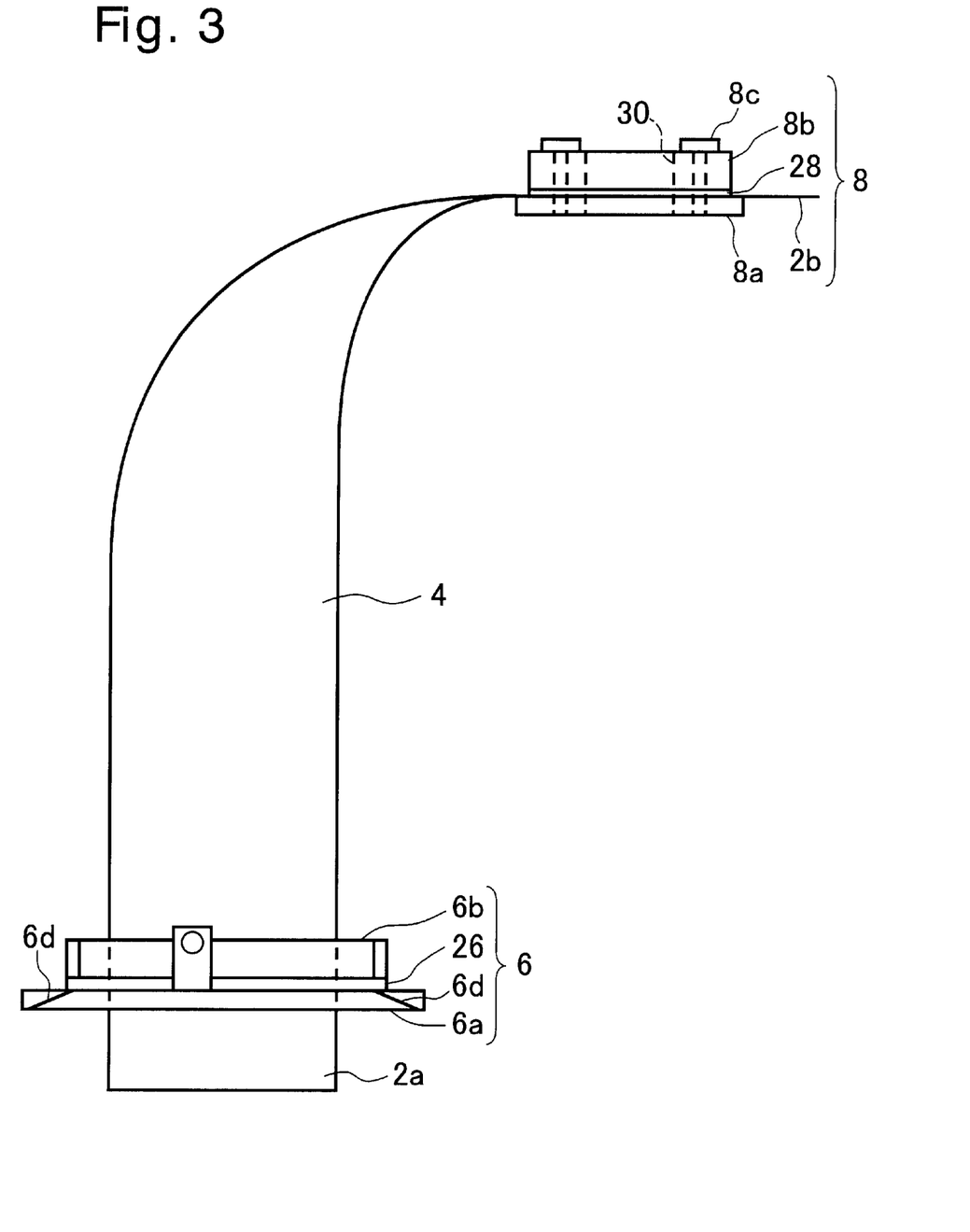
FIG. 3 is a left side elevational view of the capillary cassette.
Figure 4:
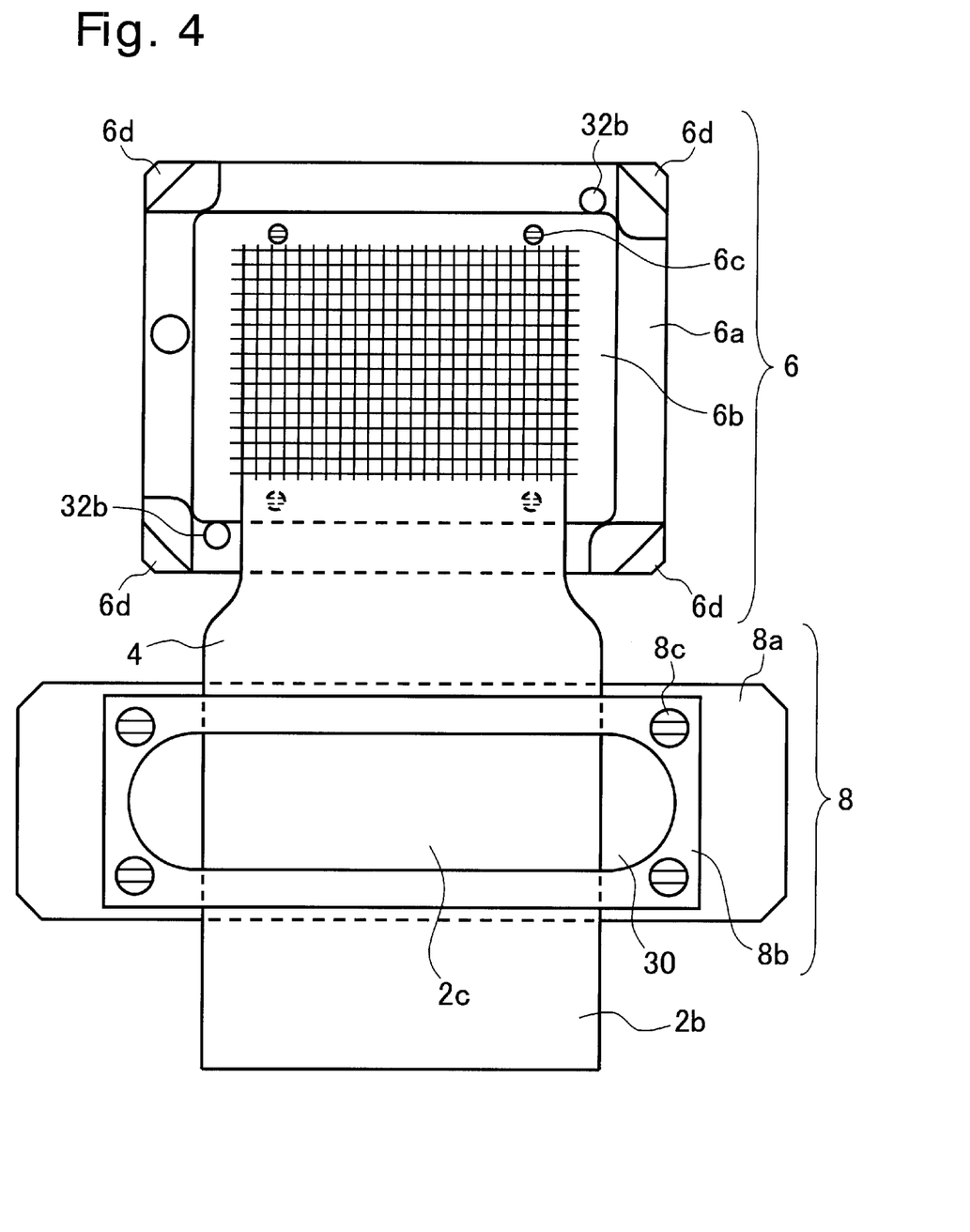
FIG. 4 is a top plan view of the capillary cassette.

FIGS. 2, 3 and 4 are schematic block diagrams of an exemplary capillary cassette mounted on a gel charger according to the present invention. FIG. 2 is a front elevational view, FIG. 3 is a left side elevational view, and FIG. 4 is a top plan view. Parts playing the same roles as those in FIG. 1 are denoted by the same reference numerals.

A sample injection side holder 6 is prepared by holding a rubber plate 26 of silicone rubber, which holds coated quartz glass capillary columns 4 in holes and fixing the same, between holder plates 6a and 6b of resin for two-dimensionally arranging the capillary columns 4, and being integrated by fixed screws 6c. The capillary columns 4 have a size of for example 300 $\mu$m in outer diameter and 100 $\mu$m in inner diameter. Each of the holder plates 6a and 6b is provided with holes for receiving 384 capillary columns 4 in 16 by 24 portions in correspondence to the positions of holes of a 384-hole. microplate employed for sample introduction. The holes of the holder plates 6a and 6b are set larger than the outer diameter of the capillary columns 4. The capillary columns 4 pass through the holder plates 6a and 6b and the rubber plate 26 held therebetween and are held in the holes of the rubber plate 26 due to the elasticity of rubber to be fixed with airtightness between the same and the holder 6.

A detection side holder 8 fixes the capillary columns 4 closely aligned with each other on a plane by holding the same with a holder plate 8a from below and with a rubber plate 28 of silicone rubber from above. A holder plate 8b fixing the rubber plate 28 to the holder plate 8a is provided on both sides of the arrangement of the capillary columns 4, in order to press and fix the capillary columns 4 against and to the holder plate 8a with the rubber plate 28. The holder plates 8a and 8b are fixed by fixing screws 8c.

The total length of the capillary columns 4 is about 500 mm, and a detected part 2c is provided on a position of about 400 mm from ends on a sample injection side. Openings 30 which are along the direction of the arrangement of the capillary columns 4 are provided on the holder plates 8a and 8b and the rubber plate 28 respectively for forming a detection window on the detected part 2c, and overlapping portions of the openings 30 define the detected part 2c. Signal detection in electrophoresis is performed through the openings 30.

The gel charger according to the present invention is provided with location pins 32a guiding the holder 6 and clamps 11 fixing the holder 6 as described later in FIG. 5, while the holder 6 is provided with location holes 32b receiving the location pins 32a and fixing parts 6d so inclined that the thicknesses of four corners are reduced outward to be engaged with the clamps 11.

Figure 5:
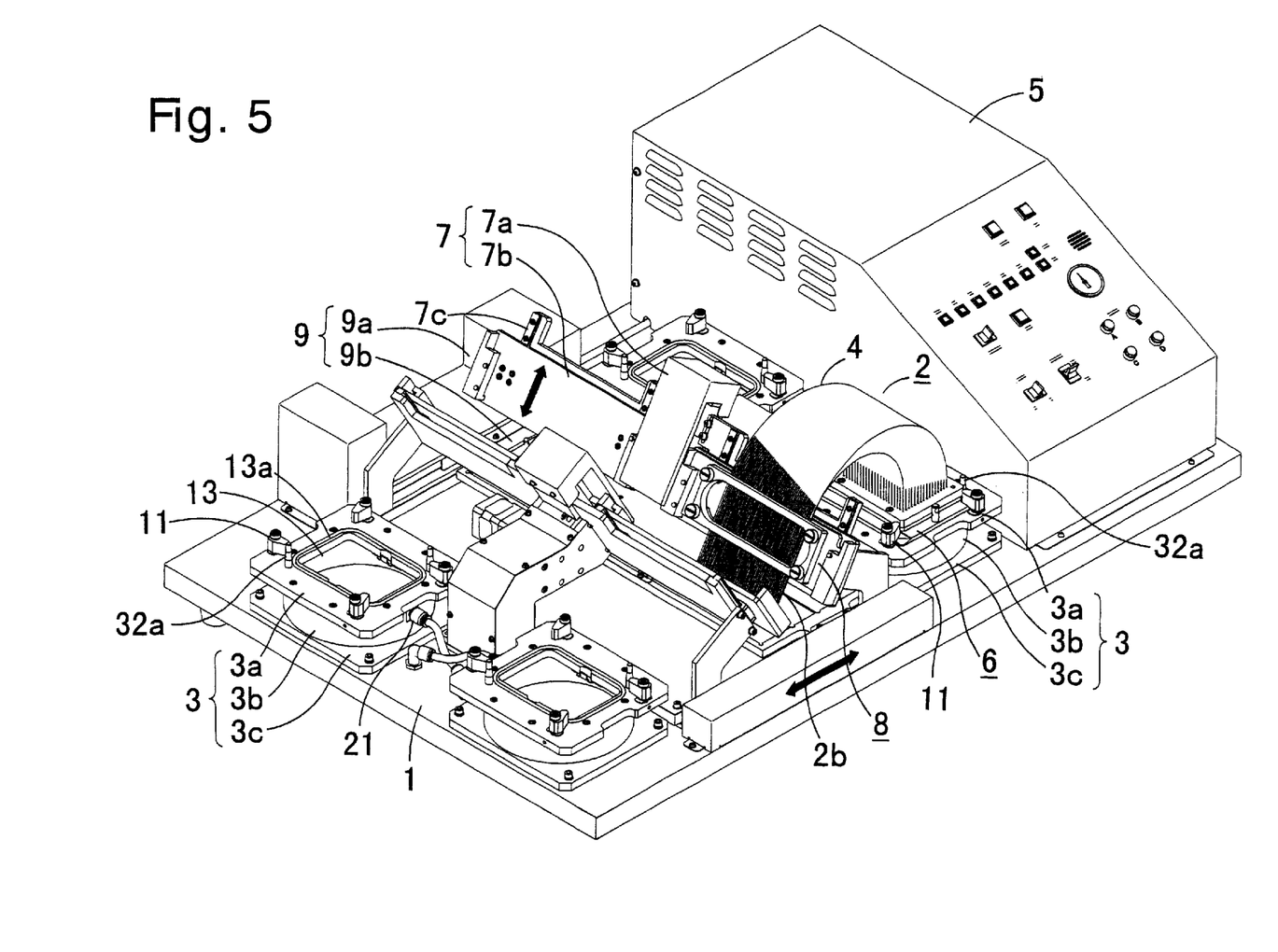
FIG. 5 is a schematic perspective view showing the whole of one embodiment.
Figure 6:
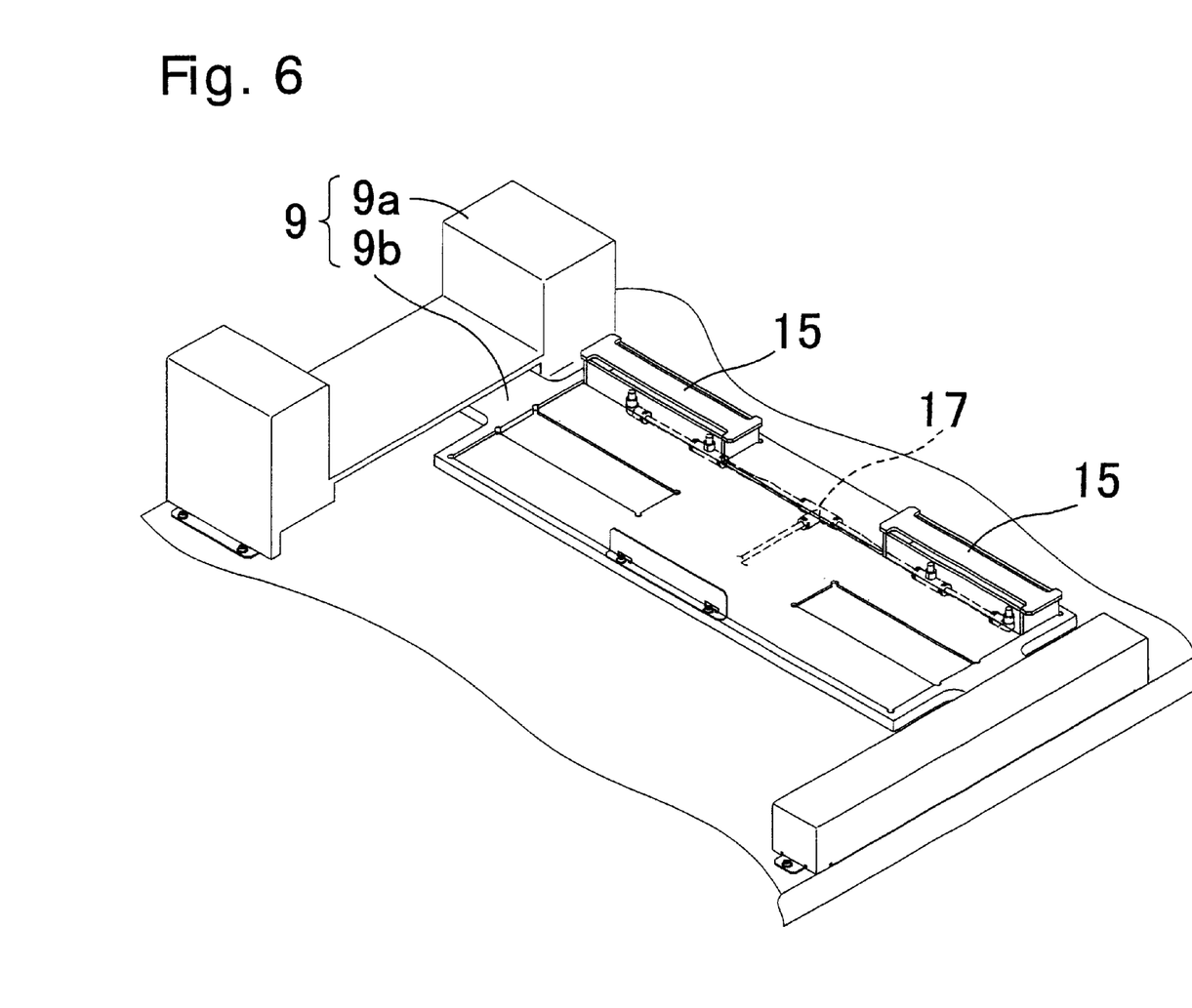
FIG. 6 is a perspective view showing a portion around a reservoir stage of an introduced substance selection mechanism of the embodiment.

FIGS. 5 and 6 are schematic block diagrams showing one embodiment of the gel charger according to the present invention. FIG. 5 is a perspective view showing the overall apparatus, and FIG. 6 is a perspective view showing a portion around a reservoir stage of an introduced substance selection mechanism of the apparatus. FIG. 6 is a piping diagram showing a passage structure of the apparatus.

Four chambers 3, in each of which the sample injection side holder 6 shown in FIGS. 2, 3 and 4 is fixed to form a closed space, a control box 5 having pressurization/decompression means pressurizing and/or decompressing the chambers 3 therein, two detection side holder up/down means 7 fixing and vertically moving detection side holders 8 and a reservoir moving mechanism 9 moving reservoirs are provided on a substrate 1.

Each chamber 3 is formed by acrylic plate 3a and 3c for closing upper and bottom portions and an acrylic pipe 3b for closing a side portion. Clearances between both ends of the acrylic pipe 3b and the acrylic plates 3a and 3c are sealed with silicone rubber packing. An opening 13 is provided on the acrylic plate 3a, for receiving the sample injection side holder 6 therein. A groove is formed around the opening 13 for fitting with an annular silicone sponge 13a having a circular section. About half the silicone sponge 13a projects from the surface of the acrylic plate 3a, to seal a clearance between the acrylic plate 3a and the holder 6. Four clamps 11 for fixing the holder 6 to the acrylic plate 3a are provided on each acrylic plate 3a, so that the holder 6 is pressed against the sponge 13a to close the space of the chamber 3 by fastening the clamps 11.

The detection side holder up/down means 7 are formed by detection side holder up/down mechanisms 7a and detection side holder fixing members 7b. Four holder fixing members 7b are provided on positions corresponding to the four chambers 3 for fixing the detection side holders 8 respectively. Adjacent pairs of holder fixing members 7b are integrated to form the holder up/down means 7 along with the holder up/down mechanisms 7a common to the holder fixing members 7b, and two such holder up/down mechanisms 7a are provided. Each holder fixing member 7b is set on the holder up/down mechanism 7a along a rail 7c provided on the holder up/down mechanism 7a to be vertically movable, as shown by thick vertical arrow. When the holder 8 is fixed to the holder fixing member 7b, an end 2b of a capillary array is vertically moved by the holder up/down mechanism 7a along with the holder fixing member 7b.

The reservoir moving mechanism 9 is formed by a reservoir stage moving mechanism 9a and a reservoir stage 9b. The reservoir stage 9b is arranged on a portion of the substrate 1 between the holder up/down mechanisms 7a to be moved toward the holder up/down mechanisms 7a by the reservoir stage moving mechanism 9a as shown by thick horizontal arrow.

Two sets of reservoirs each including a dry chamber 15 as well as an acidic solution reservoir (not shown), an alkaline solution reservoir (not shown), a clean water reservoir (not shown) and a drain reservoir (not shown) are arranged on the reservoir stage 9b in a direction perpendicular to the direction of movement thereof. The dry chamber 15 is supplied with nitrogen gas through a nitrogen gas line 17, the acidic solution reservoir stores an acidic solution, the alkaline solution reservoir stores an alkaline solution and the clean water reservoir stores pure water. These reservoirs are larger in width than the end 2b of the capillary array, which is inserted in any reservoir when the holder fixing member 7b is moved down. Each reservoir is common on the ends 2b of the capillary arrays 2 fixed to the holder fixing members 7b on opposite positions.

An upper opening of the dry chamber 15 is covered with a cover, which is provided with a slit receiving the end 2b of the capillary array for suppressing mixing of the air and the supplied nitrogen gas. The dry chamber 15 is supplied with the nitrogen gas at need from a nitrogen gas supply mechanism (not shown) through a filter 19 and a two way electromagnetic valve SV8 provided on the nitrogen gas line 17 (see FIG. 7). The filter 19 of about 10 $\mu$m, for example, prevents contamination with dirt or dust from a pipe, a cylinder or the like, for avoiding blocking of capillary columns 4 when the nitrogen gas is inhaled from the dry chamber 15 into the capillary columns 4.

An introduced substance selection mechanism according to the present invention is formed by the detection side holder up/down means 7, the reservoir moving mechanism 9, the dry chamber 15, the acidic solution reservoir, the alkaline solution reservoir, the clean water reservoir and the drain reservoir.

Movement of the holder fixing member 7b and the stage 9b is implemented by for example motors and belts provided on the holder up/down mechanism 7a and the stage moving mechanism 9a respectively. Alternatively, movement of the holder fixing member 7b and the reservoir stage 9b may be for example implemented by an air-cylinder utilizing the nitrogen gas pressure of the nitrogen gas line 17.

Figure 7:
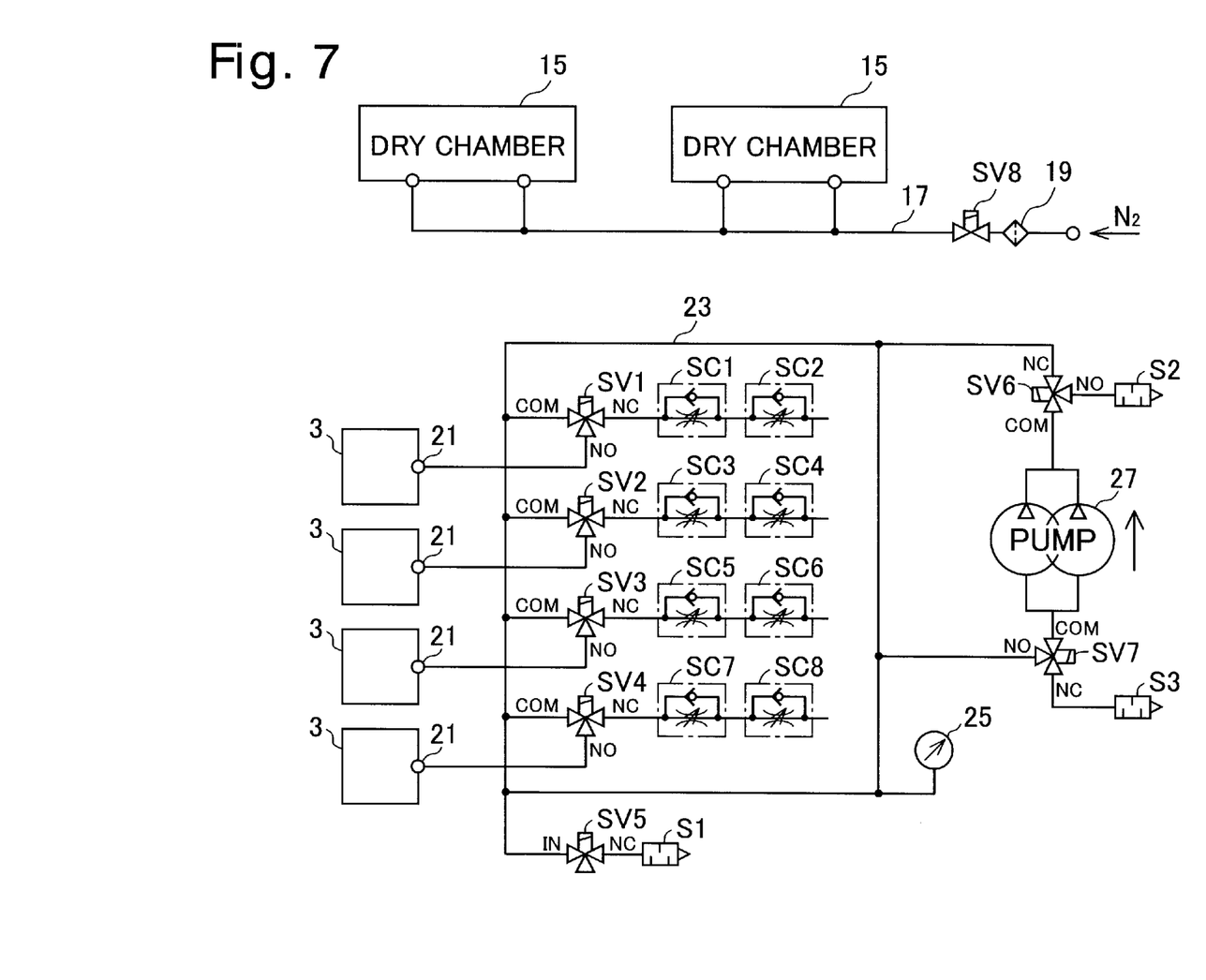
FIG. 7 is a piping diagram showing a passage structure of the embodiment

A passage structure for pressurizing and/or decompressing the chambers 3 shall now be described with reference to FIGS. 5 and 7.

In the four chambers 3, joints (gas ports) 21 are provided on side surfaces (cylindrical surfaces) of the acrylic pipes 3b respectively. Passages from the joints 21 are guided into the control box 5 through pipes provided in the substrate 1, and connected to NO (normally open) sides of three-way electromagnetic valves SV1, SV2, SV3 and SV4 provided in the control box 5. Among remaining ports of the electromagnetic valves SV1, SV2, SV3 and SV4, COM (common) sides are connected to a passage 23 common to these electromagnetic valves SV1 to SV4 while NC (normally close) sides of the electromagnetic valves SV1 to SV4 are open to the air through pairs of speed controllers SC1 and SC2, SC3 and SC4, SC5 and SC6 and SC7 and SC8 respectively. The speed controllers SC1 to SC8 are adjusted to have passage resistance of the same magnitude as that in the case where capillary cassettes are mounted on the chambers 3.

The passage 23 is connected to the NC side of the three-way electromagnetic valve SV6, connected to a discharge side of a pump 27 through the electromagnetic valve SV6, connected to the NO side of the three-way electromagnetic valve SV7 and connected to a suction side of the pump 27 through the electromagnetic valve SV6. The pump 27 is connected to the COM sides of the electromagnetic valves SV6 and SV7. Silencers S2 and S3 are connected to the NO side of the electromagnetic valve SV6 and the NC side of the electromagnetic valve SV7 respectively. The electromagnetic valves SV6 and SV7 are switched to the NO sides thereby exhausting the passage 23 through the pump 27, while the electromagnetic valves SV6 and SV7 are switched to the NC sides thereby pressurizing the passage 23 with the pump 27.

A silencer S1 is connected to the passage 23 through the electromagnetic valve SV5, so that the passage 23 can be open to the air by opening the electromagnetic valve SV5. The passage 23 is further connected with a compound pressure gauge 25 measuring the pressure therein.

The control box 5 stores a microprocessor (not shown) controlling operations of the pump 27, the electromagnetic valves SV1 to SV8, the detection side holder up/down mechanism 7a and the reservoir stage moving mechanism 9a.

Operations shall now be described. In this embodiment, a capillary cassette having the 384 capillary columns 4 shown in FIGS. 2 to 4 is employed.

An acidic solution reservoir storing a hydrochloric acid solution, an alkaline solution reservoir storing a sodium hydroxide solution, a clean water reservoir storing pure water and a vacant drain reservoir are arranged on prescribed positions of the reservoir stage 9b.

The detection side holder 8 is fixed to the holder fixing member 7b, which is located on an upper position, of the detection side holder up/down means 7. The fixing parts 6d on four corners of the holder 6 are fixed by the four clamps 11 provided on the acrylic plate 3a and these clamps 11 are fastened thereby pressing the holder 6 against the silicone sponge 13a and closely fixing the same to the acrylic plate 3a.

First, the reservoir stage moving mechanism 9a moves the reservoir stage 9b for moving the alkaline solution reservoir to a position under the end 2b of the capillary array.

The holder up/down mechanism 7a moves the fixing member 7b downward for moving the end 2b of the capillary array to a lower position and dipping the same in the sodium hydroxide solution in the alkaline solution reservoir.

Among the electromagnetic valves SV1, SV2, SV3 and SV4, that connected with the chamber 3 provided with the holder 6 for the capillary cassette is connected to the NO side and those for the chambers 3 provided with no capillary cassettes are connected to the NC sides, while the electromagnetic valves SV6 and SV7 are connected to the NO sides for working the pump 27 and decompressing the chamber 3. At this time, those of the electromagnetic valves SV1 to SV4 connected with unused chambers 3 are connected to the NC sides and opened to the air through the speed controllers SC1 and SC2, SC3 and SC4, SC5 and SC6 or SC7 and SC8. Thus, the speed controllers SC1 and SC2, SC3 and SC4, SC5 and SC6 or SC7 and SC8 obtain piping resistance equivalent to that of the chamber 3 provided with the capillary cassette. Due to this structure, the same pressures as those obtained when provided with the capillary cassettes are regularly generated in the four chambers 3.

The capillary columns 4 forming the capillary array are decompressed due to decompression of the chamber 3, for sucking the sodium hydroxide solution from the end 2b of the capillary array. The sodium hydroxide solution is introduced into the capillary columns, for discharging dirt in the capillary columns into the chamber 3 from the sample injection side along with sodium hydroxide.

After a lapse of a prescribed time, the pump 27 is stopped and the electromagnetic valve SV5 is opened to open the chamber 3 to the air. Thereafter the holder up/down mechanism 7a moves the end 2b of the capillary array to an upper position for extracting the end 2b of the capillary array from the alkaline solution reservoir.

Alkali treatment is completed through these operations.

Next, the reservoir stage moving mechanism 9a moves the reservoir stage 9b for moving the clean water reservoir to a position under the end 2b of the capillary array, in order to perform washing with pure water.

The holder up/down mechanism 7a moves the fixing member 7b downward for moving the end 2b of the capillary array to a lower position and dipping the same in the pure water in the clean water reservoir.

Thereafter the chamber 3 is decompressed similarly to the operation in the alkali treatment, for sucking the pure water from the end 2b of the capillary array. The pure water is thus introduced into the capillary columns and sodium hydroxide is discharged from the capillary columns into the chamber 3 along with the pure water.

After a lapse of a prescribed time, the pump 27 is stopped to open the chamber 3 to the air. Thereafter the holder up/down mechanism 7a moves the end 2b of the capillary array to the upper position for extracting the end 2bof the capillary array from the clean water reservoir.

Washing is completed through these operations.

Next, the reservoir stage moving mechanism 9a moves the reservoir stage 9b for moving the dry chamber 15 to a position under the end 2b of the capillary array for performing drying.

The holder up/down mechanism 7a moves the fixing member 7b downward for moving the end 2b of the capillary array to the lower position and inserting the same in the dry chamber 15 through the slit.

The electromagnetic valve SV8 of the nitrogen gas line 17 is opened for supplying nitrogen gas to the dry chamber 15 through the filter 19.

Thereafter the chamber 3 is decompressed similarly to the operation in the alkali treatment, for sucking the nitrogen gas from the end 2b of the capillary array. The nitrogen gas is thus introduced into the capillary columns for drying the capillary columns.

After a lapse of a prescribed time, the pump 27 is stopped to open the chamber 3 to the air. Thereafter the electromagnetic valve SV8 of the nitrogen gas line 17 is closed and the holder up/down mechanism 7a moves the end 2b of the capillary array to the upper position for extracting the end 2b of the capillary array from the dry chamber 15.

Drying is completed through these operations.

Next, the reservoir stage moving mechanism 9a moves the reservoir stage 9b for moving the acidic solution reservoir to a position under the end 2b of the capillary array for performing acid treatment.

The holder up/down mechanism 7a moves the fixing member 7b downward for moving the end 2b of the capillary array to the lower position and dipping the same in the hydrochloric acid solution in the acidic solution reservoir.

Thereafter the chamber 3 is decompressed similarly to the operation in the alkali treatment for sucking the hydrochloric acid solution from the end 2b of the capillary array. The hydrochloric solution is thus introduced into the capillary columns for arranging states of silanol groups present on inner wall surfaces of the capillary columns with the hydrochloric acid solution.

After a lapse of a prescribed time, the pump 27 is stopped to open the chamber 3 to the air. Thereafter the holder up/down mechanism 7a moves the end 2b of the capillary array to the upper position for extracting the end 2b of the capillary array from the acid solution reservoir.

Acid treatment is completed through these operations.

Next, operations similar to those for washing after the aforementioned alkali treatment are performed for discharging the hydrochloric acid solution from the capillary columns, and thereafter operations similar to those for drying after the aforementioned washing are performed for drying the capillary columns.

After these operations, the clamps 11 are loosened for detaching the holder 6 from the acrylic plate 3a and a solution remaining-in the chamber 3 is discharged with an aspirator or the like. Alternatively, a container (not shown) may be provided in the chamber 3 for extracting the remaining solution from the chamber 3 with the container.

Then, a gel container (not shown) storing a gel is arranged in the chamber 3. Thereafter,. the holder 6 is mounted on the acrylic plate 3a again and the clamps 11 are fastened to close the chamber 3. At this time, the length of portions of the capillary columns projecting from the holder 6 and the height of the gel container storing the gel are adjusted so that forward ends of all capillary columns on the sample injection side are dipped in the gel of the gel container.

Then, the reservoir stage moving mechanism 9a moves the reservoir stage 9b for moving the drain reservoir to a position under the end 2b of the capillary array to perform gel charging.

The holder up/down mechanism 7a moves the fixing member 7b downward for moving the end 2b of the capillary array to the lower position and inserting the same in the drain reservoir.

Among the electromagnetic valves SV1, SV2, SV3 and SV3, that connected with the chamber 3, provided with the holder 6 for the capillary cassette, is connected to the NO side and those for the chambers 3 provided with no capillary cassettes are connected to the NC sides, while the electromagnetic valves SV6 and SV7 are connected to the NC sides for working the pump 27 and pressurizing the chamber 3. At this time, those of the electromagnetic valves SV1 to SV4 connected with unused chambers 3. are connected to the NC sides and opened to the air through the speed controllers SC1 and SC2, SC3 and SC4, SC5 and SC6 or SC7 and SC8. Thus, the speed controllers SC1 and SC2, SC3 and SC4, SC5 and SC6 or SC7 and SC8 obtain piping resistance equivalent to that of the chamber 3 provided with the capillary cassette.

The chamber 3 is pressurized for forcing the gel into the capillary columns. The capillary columns are charged with the gel, while the drain reservoir receives an excess amount of gel overflowing the detection side.

After a lapse of a prescribed time, the pump 27 is stopped and the chamber 3 is opened to the air. Thereafter the holder up/down mechanism 7a moves the end 2b of the capillary array to the upper position for extracting the same from the drain reservoir.

Gel charging is completed through these operations.

While gel charging is performed by press fitting by pressurization in this embodiment, the gel container storing the gel may alternatively be arranged on the reservoir stage 9b for sucking and charging the gel by decompression.

The aforementioned operations of acid treatment, alkali treatment, washing and drying are preferably performed by automatically controlling operations of the pump 27, the electromagnetic valves SV6 to SV7, the detection side holder up/down mechanism 7a and the reservoir stage moving mechanism 9a. Consequently, the labor of an operator can be saved.

While this embodiment is of a pump storage type, it is preferable to employ a high-pressure cylinder or a vacuum pump, separately comprising a pressure generation source when the gel to be charged is that having high viscosity such as a high polymer and a high pressure must be generated.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A gel charger for charging a capillary cassette in which ends on a sample injection side of a plurality of capillary columns mounted on a multi-capillary electrophoretic apparatus are two dimensionally arranged through a holding member of a holder and fixed with airtightness between the capillary columns and the holding member, with a gel serving as a medium for electrophoresing samples, comprising:

a chamber airtightly fixing the ends on the sample injection side of all the capillary columns of the capillary cassette through the holder, the chamber being adapted for successively introducing an acidic solution, pure water and inert gas into the capillary columns by decompression or pressurization for arranging inner parts of all the capillary columns and therefore introducing the gel into all the capillary columns by decompression or pressurization, wherein the chamber has an opening on its upper surface, with the opening having a closure means receiving the ends on the sample injection side of the capillary columns therein and closing the opening, and the chamber further has a gas outlet, the gel charger further comprising:

an inert gas supply mechanism supplying inert gas, an introduced substance selection mechanism provided with an inert gas supply port supplied with inert gas from the inert gas supply mechanism, an acidic solution container storing an acidic solution, a pure water container storing pure water and a gel container storing the gel, and comprising a moving mechanism moving the inert gas supply port, the acidic solution container, the pure water container and the gel container as well as ends of the capillary columns on a detection side opposite to the sample injection side so that the ends of the capillary columns on the detection side are inserted in any of the inert gas supply port, the acidic solution container, the pure water container and the gel container, and a decompression mechanism provided on the gas outlet of the chamber.

2. The gel charger in accordance with claim 1, wherein the introduced substance selection mechanism further comprises an alkaline solution container storing an alkaline solution, and the moving mechanism moves the inert gas supply port, the acidic solution container, the alkaline solution container, the pure water container and the gel container as well as the ends of the capillary columns on the detection side so that the ends of the capillary columns on the detection side are dipped in any of the inert gas supply port, the acidic solution container, the alkaline solution container, the pure water container and the gel container.

3. A gel charger for charging a capillary cassette in which ends on a sample injection side of a plurality of capillary columns mounted on a multi-capillary electrophoretic apparatus are two dimensionally arranged through a holding member of a holder and fixed with airtightness between the capillary columns and the holding member, with a gel serving as a medium for electrophoresing samples, comprising:

a chamber airtightly fixing the ends on the sample injection side of all the capillary columns of the capillary cassette through the holder, the chamber being adapted for successively introducing an acidic solution, pure water and inert gas into the capillary columns by decompression or pressurization for arranging inner parts of all the capillary columns and therefore introducing the gel into all the capillary columns by decompression or pressurization wherein the chamber has an opening on its upper surface, with the opening having a closure means receiving the ends on the sample injection side of the capillary columns therein and closing the opening, and the chamber further has a gas outlet, the gel charger further comprising:

a gel container, storing the gel in a position where the ends on the sample injection side of the capillary columns are dipped while the opening of the chamber is closed with the holder, detachably arranged in the chamber, an inert gas supply mechanism supplying inert gas, an introduced substance selection mechanism provided with an inert gas supply port supplied with inert gas from the inert gas supply mechanism, an acidic solution container storing an acidic solution, a pure water container storing pure water and a drain container and comprising a moving mechanism moving the inert gas supply port, the acidic solution container, the pure water container and the drain container as well as ends of the capillary columns on a detection side opposite to the sample injection side so that the ends of the capillary columns on the detection side are inserted in any of the inert gas supply port, the acidic solution container, the pure water container and the drain container, and a pressurization/decompression mechanism provided on the gas outlet of the chamber.

4. The gel charger in accordance with claim 3, wherein the introduced substance selection mechanism further comprises an alkaline solution container storing an alkaline solution, and the moving mechanism moves the inert gas supply port, the acidic solution container, the alkaline solution container, the pure water container and the drain container as well as the ends of the capillary columns on the detection side so that the ends of the capillary columns on the detection side are dipped in any of the inert gas supply port, the acidic solution container, the alkaline solution container, the pure water container and the drain container.

5. The gel charger in accordance with claim 1, comprising a plurality of the chambers for sharing the decompression mechanism with the plurality of chambers and sharing the introduced substance selection mechanism as to the capillary columns mounted on the different chambers.

6. The gel charger in accordance with claim 3, comprising a plurality of the chambers for sharing the decompression mechanism with the plurality of chambers and sharing the introduced substance selection mechanism as to the capillary columns mounted on the different chambers.

7. The gel charger in accordance with claim 1, comprising a control part automatically controlling operations of the inert gas supply mechanism, the introduced substance selection mechanism and the decompression mechanism.

8. The gel charger in accordance with claim 3, comprising a control part automatically controlling operations of the inert gas supply mechanism, the introduced substance selection mechanism and the pressurization/decompression mechanism.

9. The gel charger in accordance with claim 5, wherein the decompression mechanism comprises a pump common to all the chambers and the respective chambers are provided with speed controllers having passage resistance of the same magnitude as that in the case provided with the capillary cassette, so that the chambers and the speed controllers are switchably connected to a passage connected with the pump.

10. The gel charger in accordance with claim 6, wherein the pressurization/decompression mechanism comprises a pump common to all the chambers and the respective chambers are provided with speed controllers having passage resistance of the same magnitude as that in the case provided with the capillary cassette, so that the chambers and the speed controllers are switchably connected to a passage connected with the pump.

11. A gel charger for charging a capillary cassette in which first ends on a sample injection side of a plurality of capillary columns mounted on a multi-capillary electrophoretic apparatus are two-dimensionally arranged through a holding member of a holder and fixed with air tightness between the capillary columns and the holding member, with a gel serving as a medium for electrophoresing samples, comprising:

a sample injection side holder retaining the plurality of capillary columns in an air tight manner with second ends disposed opposite the first ends depending downwardly therefrom;

a plurality of chambers;

means for containing at least an acidic solution, water and the gel;

a source of inert gas associated with at least the chambers;

means for moving the plurality of capillary columns such that the ends of the capillary columns are sequentially immersed in the acidic solution, the water and the gel while the sample injection side holder is sealably engaged with respective ones of the chambers;

means for drawing the acid solution, the water and the gel into the plurality of capillary columns through the ends by pressurization or decompression while the sample injection side holder is sealably engaged with respective ones of the chambers; and means for injecting the inert gas through the plurality of capillary columns after being immersed in and drawn with the respective acid solution and water until the plurality of capillary columns are dried by the injected inert gas.

12. A gel charger for charging a capillary cassette in which ends on a sample injection side of a plurality of capillary columns mounted on a multi-capillary electrophoretic apparatus are two-dimensionally arranged through a holding member of a holder and fixed with airtightness between the capillary columns and the holding member, with a gel serving as a medium for electrophoresing samples, comprising:

a plurality of chambers, each chamber airtightly fixing the ends on the sample injection side of all the capillary columns of the capillary cassette through the holder, each chamber being adapted for successively introducing an acidic solution, pure water and inert gas into the capillary columns by decompression or pressurization for arranging inner parts of all the capillary columns and thereafter introducing the gel into all the capillary columns by decompression or pressurization, each chamber having an opening on its upper surface, with the opening having a closure means receiving the ends on the sample injection side of the capillary columns therein and closing the opening, and each chamber having a gas outlet;

an inert gas supply mechanism supplying inert gas;

an introduced substance selection mechanism provided with an inert gas supply port supplied with inert gas from the inert gas supply mechanism, an acidic solution container storing an acidic solution, a pure water container storing pure water and a gel container storing the gel, and including a moving mechanism moving the inert gas supply port, the acidic solution container, the pure water container and the gel container as well as ends of the capillary columns on a detection side opposite to the sample injection side so that the ends of the capillary columns on the detection side are inserted in any of the inert gas supply port, the acidic solution container, the pure water container and the gel container; and a decompression mechanism provided on the gas outlet of the chamber, wherein the plurality of the chambers share the decompression mechanism and share the introduced substance selection mechanism as to the capillary columns mounted on the different chambers and the decompression mechanism includes a pump common to all the chambers and the respective chambers are provided with speed controllers having passage resistance of the same magnitude as that in the case provided with the capillary cassette, so that the chambers and the speed controllers are switchably connected to a passage connected with the pump.

13. The gel charger in accordance with claim 12, wherein the introduced substance selection mechanism further comprises an alkaline solution container storing an alkaline solution, and the moving mechanism moves the inert gas supply port, the acidic solution container, the alkaline solution container, the pure water container and the gel container as well as the ends of the capillary columns on the detection side to that the ends of the capillary columns on the detection side are dipped in any of the inert gas supply port, the acidic solution container, the alkaline solution container, the pure water container and the gel container.

14. The gel charger in accordance with claim 12, further comprising a control part automatically controlling operations of the inert gas supply mechanism, the introduced substance selection mechanism and the decompression mechanism.

15. A gel charger for charging a capillary cassette in which ends on a sample injection side of a plurality of capillary columns mounted on a multi-capillary electrophoretic apparatus are two-dimensionally arranged through a holding member of a holder and fixed with airtightness between the capillary columns and the holding member, with a gel serving as a medium for electrophoresing samples, comprising:

a plurality of chambers, each chamber airtightly fixing the ends on the sample injection side of all the capillary columns of the capillary cassette through the holder, each chamber being adapted for successively introducing an acidic solution, pure water and inert gas into the capillary columns by decompression or pressurization for arranging inner parts of all the capillary columns and thereafter introducing the gel into all the capillary columns by decompression or pressurization, each chamber having an opening on its upper surface, with the opening having a closure means receiving the ends on the sample injection side of the capillary columns therein and closing the opening, and each chamber having a gas outlet;

a gel container, storing the gel in the position where the ends on the sample injection side of the capillary columns are dipped while the opening of the chamber is closed with the holder, detachably arranged in the chamber;

an inert gas supply mechanism supplying inert gas;

an introduced substance selection mechanism provided with an inert gas supply port supplied with inert gas from the inert gas supply mechanism, an acidic solution container storing an acidic solution, a pure water container storing pure water and a drain container and including a moving mechanism moving the inert gas supply port, the acidic solution container, the pure water container and the drain container as well as ends of the capillary columns on a detection side opposite to the sample injection side so that the ends of the capillary columns on the detection side are inserted in any of the inert gas supply port, the acidic solution container, the pure water container and the drain container; and a pressurization/decompression mechanism provided on the gas outlet of the chamber, wherein the plurality of the chambers share the decompression mechanism and share the introduced substance selection mechanism as to the capillary columns mounted on the different chambers and the pressurization/decompression mechanism including a pump common to all the chambers and the respective chambers are provided with speed controllers having passage resistance of the same magnitude as that in the case provided with the capillary cassette, so that the chambers and the speed controllers are switchably connected to a passage connected with the pump.

16. The gel chamber in accordance with claim 15, wherein the introduced substance selection mechanism further comprises an alkaline solution container storing an alkaline solution, and the moving mechanism moves the inert gas supply port, the acidic solution container, the alkaline solution container, the pure water container and the drain container as well as the ends of the capillary columns on the detection side so that the ends of the capillary columns on the detection side are dipped in any of the inert gas supply port, the acidic solution container, the alkaline solution container, the pure water container and the drain container.

17. The gel charger in accordance with claim 15, further comprising a control part automatically controlling operations of the inert gas supply mechanism, the introduced substance selection mechanism and the pressurization/decompression mechanism.

* * * * *

UNITED STATES PATENT AND TRADEMARK OFFICE
CERTIFICATE OF CORRECTION

PATENT NO.    : 6,428,670 B1
DATED         : August 6, 2002
INVENTOR(S)   : Yoshihide Hayashizaki et al.

It is certified that error appears in the above-identified patent and that said Letters Patent is hereby corrected as shown below:

<u>Title page,</u>
The assignees should read:

-- [73] Assignees: The Institute of Physical and Chemical Research, Saitama; Shimadzu Corporation, Kyoto; Japan Science and Technology Corporation, Saitama, all of (JP) --

Signed and Sealed this

Twentieth Day of May, 2003

JAMES E. ROGAN
*Director of the United States Patent and Trademark Office*